United States Patent
Betancourt Villamizar et al.

(10) Patent No.: US 10,716,820 B2
(45) Date of Patent: Jul. 21, 2020

(54) COMPOSITION FOR TREATMENT OF OXIDATIVE STRESS AND CARDIOVASCULAR DISEASE

(71) Applicant: TEAM FOODS COLOMBIA S.A., Bogota (CO)

(72) Inventors: Eddy Carolina Betancourt Villamizar, Bogota (CO); Juan Fernando Murcillo Rojas, Bogota (CO); Rubén Dario Betancourt Cortés, Bogota (CO)

(73) Assignee: Team Foods Colombia S.A., Bogota (CO)

( * ) Notice: Subject to any disclaimer, the term of this patent is extended or adjusted under 35 U.S.C. 154(b) by 0 days.

(21) Appl. No.: 15/571,259

(22) PCT Filed: Jun. 5, 2015

(86) PCT No.: PCT/IB2015/000870
§ 371 (c)(1),
(2) Date: Nov. 1, 2017

(87) PCT Pub. No.: WO2016/189345
PCT Pub. Date: Dec. 1, 2016

(65) Prior Publication Data
US 2018/0344794 A1    Dec. 6, 2018

Related U.S. Application Data

(60) Provisional application No. 62/165,669, filed on May 22, 2015.

(51) Int. Cl.
*A61K 36/88* (2006.01)
*A61K 36/31* (2006.01)
(Continued)

(52) U.S. Cl.
CPC ............. *A61K 36/31* (2013.01); *A61K 31/07* (2013.01); *A61K 31/575* (2013.01); *A61K 31/59* (2013.01);
(Continued)

(58) Field of Classification Search
CPC ..................................................... A61K 36/88
See application file for complete search history.

(56) References Cited

U.S. PATENT DOCUMENTS

2008/0305096 A1    12/2008    Verdegem et al.

FOREIGN PATENT DOCUMENTS

| CN | 101 755 926 A | 6/2010 |
|----|---------------|--------|
| CN | 101 766 235 A | 7/2010 |

(Continued)

OTHER PUBLICATIONS

Zwaka, et al., "C-Reactive Protein-Mediated Low Density Lipoprotein Uptake by Microphages; Implications for Atherosclerosis," Circulation, 2001, vol. 103, No. 9, pp. 1194-1197.
(Continued)

*Primary Examiner* — Rosanne Kosson
(74) *Attorney, Agent, or Firm* — BakerHostetler

(57) ABSTRACT

The present invention, in some embodiments, is a composition that includes 35 to 50 weight percent of a first vegetable oil having a saturated fatty acid content of 4% to 12%, 35 to 50 weight percent of a second vegetable oil having an alpha-linolenic acid content of 45% to 65%, 0.005 to 0.15 weight percent of at least one of Vitamin A and Vitamin D, 2 to 10 weight percent of at least one phytosterol; and 0.02 to 0.2 weight percent of an antioxidant including, but not limited to, tocopherol, ascorbyl palmitate, Rosemary extract and mixtures thereof. The present invention further includes, in some embodiments, us of a composition for treating oxidative stress and cardiovascular diseases.

9 Claims, 7 Drawing Sheets

(51) Int. Cl.
     *A61K 31/07*    (2006.01)
     *A61K 31/575*   (2006.01)
     *A61K 31/59*    (2006.01)
     *A61K 36/53*    (2006.01)
     *A61K 36/55*    (2006.01)
     *A61P 3/04*     (2006.01)

(52) U.S. Cl.
     CPC .............. *A61K 36/53* (2013.01); *A61K 36/55* (2013.01); *A61P 3/04* (2018.01)

(56) References Cited

FOREIGN PATENT DOCUMENTS

| CN | 101 766 236 A | 7/2010 | |
| CN | 103 156 003 A | 6/2013 | |
| WO | WO-2015130631 A1 * | 9/2015 | ............... A23D 9/02 |

OTHER PUBLICATIONS

Elahi, et al., "Oxidative Stress as a Mediator of Cardiovascular Disease," Oxidative Medicine and Cellular Longevity 2:5, Nov./Dec. 2009, pp. 259-269.

Lakshmi, et al., "Oxidative Stress in Cardiovascular Disease," Indian Journal of Biochemistry & Biophysics, vol. 46, Dec. 2009, pp. 421-440.

Cai, et al., "Endothelial Dysfunction in Cardiovascular Diseases; The Role of Oxidant Stress," Circulation Research, 2000, vol. 87, No. 10, pp. 840-844.

Leah G. Gillingham et al., "High-oleic rapeseed (canola) and flaxseed oils modulate serum lipids and inflammatory biomarkers in hypercholesterolaemic subjects," British Journal of Nutrition, vol. 105, No. 3, Sep. 29, 2010, pp. 417-427, XP055229367.

* cited by examiner

Caenorhabditis elegans as a Heart Disease Model

**A. Advantages of *C elegans* mutant analysis**

Inexpensive and easy to culture

Fast generation time (3 d)

Large brood size (about 300)

Mutants can be frozen indefinitely and revived

Multiple successful mutagenesis strategies

Rapid out-crossing for removing secondary mutations

Fine structure mapping of mutations

Rapid mapping by deletion and deficiency arrays

Rapid and inexpensive correlation of mutations to the small genome sequence

High throughput screening by RNAi knockdowns in live nematodes

Rapid construction of transgenic and transformed nematodes

Rapid transgenic rescue of mutants

**B. Advantages of *C elegans* for studying heart muscle**

Body wall muscle is striated like cardiac muscle

Extensive conservation of sarcomere structure and components

Body wall muscle required for locomotion but not viability

Optical transparency permits visualization of muscle structure in live animals

Self-fertilization allows propagation of mutants that are unable to mate

Purification of specific muscle proteins and myofilaments

**C. Limitations of *C elegans* as a specific heart disease model**

No heart or vascular system

Body wall muscle is striated but not specifically cardiac

Body wall muscle expresses some specialized versions of myofilament arrays, membrane adhesion sites and their proteins distinct from their homologs in cardiac muscle Body wall muscle dense bodies serve the function of both Z-disks and costameres

FIG. 7

COMPOSITION FOR TREATMENT OF OXIDATIVE STRESS AND CARDIOVASCULAR DISEASE

RELATED APPLICATIONS

This application is a National Stage of International patent application PCT/IB2015/000870, filed on Jun. 5, 2015, which claims the priority of U.S. provisional application Ser. No. U.S.S.N. 62/165,669, entitled "Composition for Treatment of Oxidative Stress and Cardiovascular Disease," filed May 22, 2015, which are incorporated herein by reference in their entirety for all purposes

BACKGROUND OF INVENTION

Oxidative stress and cardiovascular diseases are known.

TECHNICAL FIELD

The present invention relates to compositions for treatment of oxidative stress and cardiovascular disease.

BRIEF SUMMARY OF INVENTION

In some embodiments, the present invention is a composition comprising 35 to 50 weight percent of a first vegetable oil having a saturated fatty acid content of 4% to 12%; 35 to 50 weight percent of a second vegetable oil having an alpha-linolenic acid content of 45% to 65%; 0.005 to 0.15 weight percent of at least one of Vitamin A and Vitamin D; 2 to 10 weight percent of at least one phytosterol; and 0.02 to 0.2 weight percent of antioxidant, wherein the antioxidant is selected from the group consisting of tocopherol, ascorbyl palmitate, Rosemary extract and mixtures thereof.

In some embodiments, the first vegetable oil is selected from the group consisting of canola oil, soybean oil, corn oil and sunflower oil. In some embodiments, the second vegetable oil is selected from the group consisting of flax seed oil, chia oil, and sacha inchi oil.

In some embodiments, the composition comprises 0.005 to 0.15 weight percent of Vitamin A and Vitamin D. In some embodiments, at least one phytosterol comprises at least one vegetable sterol. In some embodiments, the composition comprises 40 to 50 weight percent of the first vegetable oil.

In some embodiments, the composition comprises 40 to 50 weight percent of the second vegetable oil. In some embodiments, the composition comprises 5 to 10 weight percent of the at least one phytosterol. In some embodiments, the composition comprises 0.1 to 0.2 weight percent of the antioxidant.

In some embodiments, the present invention is a method of treatment of oxidative stress comprising orally administering an effective amount to a human of a composition so as to result in reduction of the levels of C reactive protein (PCR) under 1.0 mg/L in blood, wherein the composition comprises: 35 to 50 weight percent of a first vegetable oil having a saturated fatty acid content of 4% to 12%; 35 to 50 weight percent of a second vegetable oil having an alpha-linolenic acid content of 45% to 65%; 0.005 to 0.15 weight percent of at least one of Vitamin A and Vitamin D; 2 to 10 weight percent of at least one phytosterol; and 0.02 to 0.2 weight percent of antioxidant, wherein the antioxidant is selected from the group consisting of tocopherol, ascorbyl palmitate, Rosemary extract and mixtures thereof.

In some embodiments, the effective amount comprises 8 to 11 grams per dose. In some embodiments, the effective amount comprises 2 doses per day.

In some embodiments, the first vegetable oil is selected from the group consisting of canola oil, soybean oil, corn oil and sunflower oil.

In some embodiments, the second vegetable oil is selected from the group consisting of flax seed oil, chia oil, and sacha inchi oil.

In some embodiments, the present invention is a composition according to any of the embodiments detailed herein for use in treatment of oxidative stress. In some embodiments, the present invention is a composition according to any of the embodiments detailed herein for use in treatment of cardiovascular disease.

In some embodiments, a composition according to any of the embodiments detailed herein, therein only such an effective amount of the composition is used so as to result in reduction of the levels of C reactive protein (PCR) under 1.0 mg/L blood.

In some embodiments, the present invention includes the use of a composition according to any of the embodiments detailed herein for the manufacture of a medicament for use in treatment of oxidative stress. In some embodiments, the present invention includes the use of a composition according to any of the embodiments detailed herein for the manufacture of a medicament for use in treatment of cardiovascular disease.

In some embodiments, the present invention includes the use of a composition according to any of the embodiments detailed herein for the manufacture of a medicament for use in treatment of oxidative stress, therein the medicament comprises an effective amount of the composition so as to result in reduction of the levels of C reactive protein (PCR) under 1.0 mg/L blood.

In some embodiments, the present invention includes the use of a composition according to any of the embodiments detailed herein for the manufacture of a medicament for use in treatment of cardiovascular disease, therein the medicament comprises an effective amount of the composition so as to result in reduction of the levels of C reactive protein (PCR) under 1.0 mg/L blood.

BRIEF DESCRIPTION OF THE DRAWINGS

FIG. 7 illustrates additional features of the C. elegans model.

Figure 1:
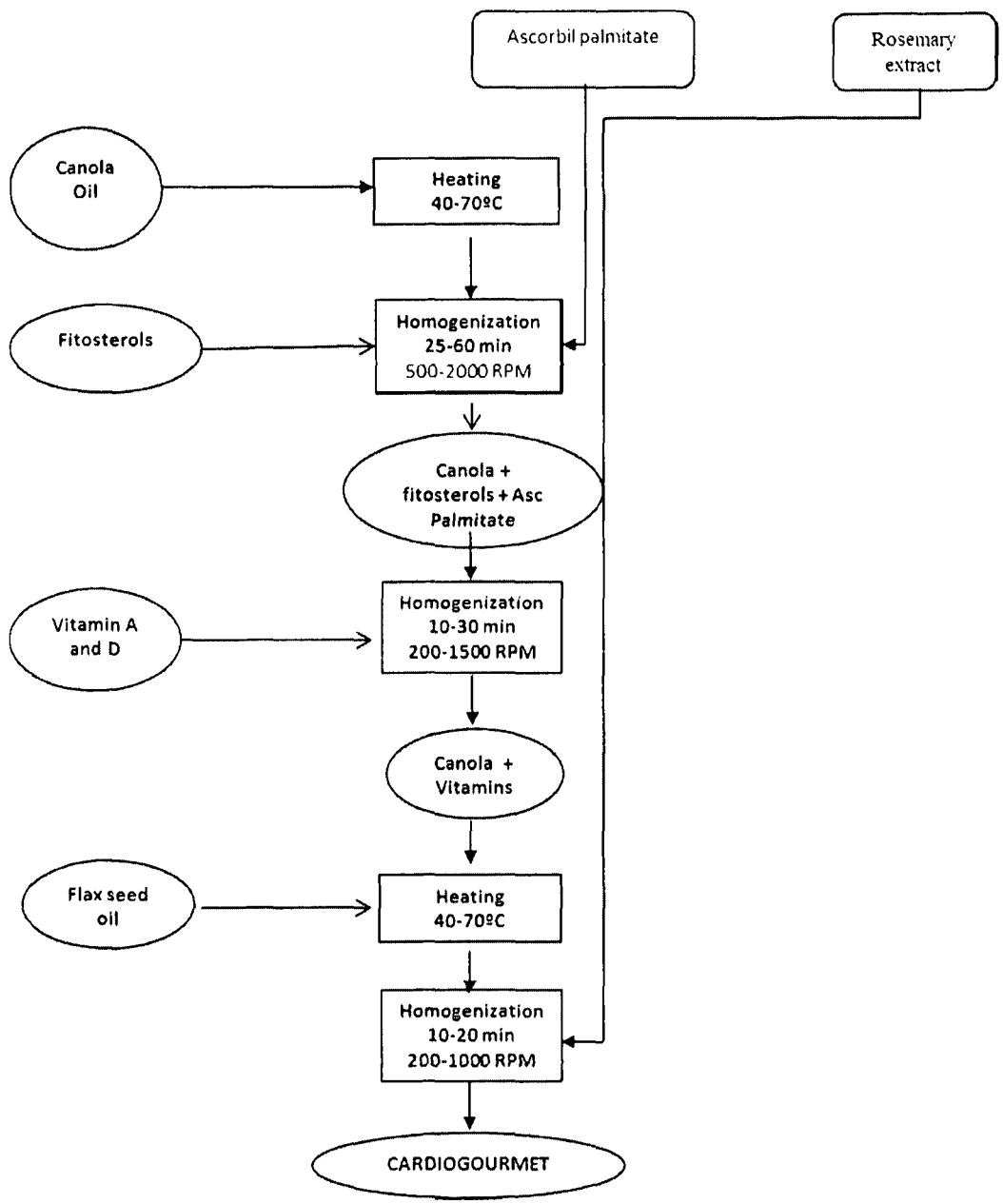
FIG. 1 illustrates a flowchart for a method of producing a composition in accordance with an embodiment of the present invention.

The figures constitute a part of this specification and include illustrative embodiments of the present invention and illustrate various objects and features thereof. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

DETAILED DESCRIPTION

The present invention will be further explained with reference to the attached drawings, wherein like structures are referred to by like numerals throughout the several views. The drawings shown are not necessarily to scale, with emphasis instead generally being placed upon illustrating the principles of the present invention. Further, some features may be exaggerated to show details of particular components.

The figures constitute a part of this specification and include illustrative embodiments of the present invention and illustrate various objects and features thereof. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

Throughout the specification and claims, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on".

In some embodiments, the present invention is a composition comprising 35 to 50 weight percent of a first vegetable oil having a saturated fatty acid content of 4% to 12%; 35 to 50 weight percent of a second vegetable oil having an alpha-linolenic acid content of 45% to 65%; 0.005 to 0.15 weight percent of at least one of Vitamin A and Vitamin D; 2 to 10 weight percent of at least one phytosterol; and 0.02 to 0.2 weight percent of antioxidant, wherein the antioxidant is selected from the group consisting of tocopherol, ascorbyl palmitate, Rosemary extract and mixtures thereof.

In some embodiments, the first vegetable oil is selected from the group consisting of canola oil, soybean oil, corn oil and sunflower oil. In some embodiments, the second vegetable oil is selected from the group consisting of flax seed oil, chia oil, and sacha inchi oil.

In some embodiments, the composition comprises 0.005 to 0.15 weight percent of Vitamin A and Vitamin D. In some embodiments, at least one phytosterol comprises at least one vegetable sterol. In some embodiments, the composition comprises 40 to 50 weight percent of the first vegetable oil.

In some embodiments, the composition comprises 40 to 50 weight percent of the second vegetable oil. In some embodiments, the composition comprises 5 to 10 weight percent of at least one phytosterol. In some embodiments, the composition comprises 0.1 to 0.2 weight percent of the antioxidant.

In some embodiments, the present invention is a method of treatment of oxidative stress comprising orally administering an effective amount to a human of a composition so as to result in reduction of the levels of C reactive protein (PCR) under 1.0 mg/L in blood, wherein the composition comprises: 35 to 50 weight percent of a first vegetable oil having a saturated fatty acid content of 4% to 12%; 35 to 50 weight percent of a second vegetable oil having an alpha-linolenic acid content of 45% to 65%; 0.005 to 0.15 weight percent of at least one of Vitamin A and Vitamin D; 2 to 10 weight percent of at least one phytosterol; and 0.02 to 0.2 weight percent of antioxidant, wherein the antioxidant is selected from the group consisting of tocopherol, ascorbyl palmitate, Rosemary extract and mixtures thereof.

In some embodiments, the effective amount comprises 8 to 11 grams per dose. In some embodiments, the effective amount comprises 2 doses per day.

In some embodiments, the first vegetable oil is selected from the group consisting of canola oil, soybean oil, corn oil and sunflower oil.

In some embodiments, the second vegetable oil is selected from the group consisting of flax seed oil, chia oil, and sacha inchi oil.

In some embodiments, the present invention is a composition according to any of the embodiments detailed herein for use in treatment of oxidative stress. In some embodiments, the present invention is a composition according to any of the embodiments detailed herein for use in treatment of cardiovascular disease.

In some embodiments, a composition according to any of the embodiments detailed herein, therein only such an effective amount of the composition is used so as to result in reduction of the levels of C reactive protein (PCR) under 1.0 mg/L blood.

In some embodiments, the present invention includes the use of a composition according to any of the embodiments detailed herein for the manufacture of a medicament for use in treatment of oxidative stress. In some embodiments, the present invention includes the use of a composition according to any of the embodiments detailed herein for the manufacture of a medicament for use in treatment of cardiovascular disease.

In some embodiments, the present invention includes the use of a composition according to any of the embodiments detailed herein for the manufacture of a medicament for use in treatment of oxidative stress, therein the medicament comprises an effective amount of the composition so as to result in reduction of the levels of C reactive protein (PCR) under 1.0 mg/L blood.

In some embodiments, the present invention includes the use of a composition according to any of the embodiments detailed herein for the manufacture of a medicament for use in treatment of cardiovascular disease, therein the medicament comprises an effective amount of the composition so as to result in reduction of the levels of C reactive protein (PCR) under 1.0 mg/L blood.

In some embodiments, the present invention is a method of treatment of cardiovascular disease comprising: orally administering an effective amount to a human of a composition so as to result in reduction of the levels of C reactive protein (PCR) under 1.0 mg/L in blood, wherein the composition comprises: 35 to 50 weight percent of a first vegetable oil having a saturated fatty acid content of 4% to 12%; 35 to 50 weight percent of a second vegetable oil having an alpha-linolenic acid content of 45% to 65%; 0.005 to 0.15 weight percent of at least one of Vitamin A and Vitamin D; 2 to 10 weight percent of at least one phytosterol; and 0.02 to 0.2 weight percent of antioxidant, wherein the antioxidant is selected from the group consisting of tocopherol, ascorbyl palmitate, Rosemary extract and mixtures thereof.

In some embodiments, the effective amount comprises 8 to 11 grams per dose. In some embodiments, the effective amount comprises 2 doses per day. In some embodiments, the first vegetable oil is selected from the group consisting of canola oil, soybean oil, corn oil and sunflower oil. In some embodiments, the second vegetable oil is selected from the group consisting of flax seed oil, chia oil, and sacha inchi oil.

A method of making the composition according to an embodiment of the present invention is shown in FIG. 1.

In some embodiments, the composition comprises 35 to 45 weight percent of a first vegetable oil having a saturated fatty acid content of 4% to 12%. In some embodiments, the composition comprises 35 to 40 weight percent of a first vegetable oil having a saturated fatty acid content of 4% to 12%. In some embodiments, the composition comprises 40 to 50 weight percent of a first vegetable oil having a saturated fatty acid content of 4% to 12%. In some embodiments, the composition comprises 45 to 50 weight percent of a first vegetable oil having a saturated fatty acid content of 4% to 12%. In some embodiments, the composition comprises 40 to 45 weight percent of a first vegetable oil having a saturated fatty acid content of 4% to 12%.

In some embodiments, the composition comprises 35 to 50 weight percent of a first vegetable oil having a saturated fatty acid content of 4% to 10%. In some embodiments, the composition comprises 35 to 50 weight percent of a first vegetable oil having a saturated fatty acid content of 4% to 8%. In some embodiments, the composition comprises 35 to 50 weight percent of a first vegetable oil having a saturated fatty acid content of 4% to 6%. In some embodiments, the composition comprises 35 to 50 weight percent of a first vegetable oil having a saturated fatty acid content of 6% to 12%. In some embodiments, the composition comprises 35 to 50 weight percent of a first vegetable oil having a saturated fatty acid content of 8% to 12%. In some embodiments, the composition comprises 35 to 50 weight percent of a first vegetable oil having a saturated fatty acid content of 10% to 12%. In some embodiments, the composition comprises 35 to 50 weight percent of a first vegetable oil having a saturated fatty acid content of 6% to 10%.

In some embodiments, the composition further comprises 35 to 45 weight percent of a second vegetable oil having an alpha-linolenic acid content of 45% to 65%. In some embodiments, the composition further comprises 35 to 40 weight percent of a second vegetable oil having an alpha-linolenic acid content of 45% to 65%.

In some embodiments, the composition further comprises 40 to 50 weight percent of a second vegetable oil having an alpha-linolenic acid content of 45% to 65%. In some embodiments, the composition further comprises 45 to 50 weight percent of a second vegetable oil having an alpha-linolenic acid content of 45% to 65%. In some embodiments, the composition further comprises 50 to 60 weight percent of a second vegetable oil having an alpha-linolenic acid content of 45% to 65%.

In some embodiments, the composition further comprises 35 to 50 weight percent of a second vegetable oil having an alpha-linolenic acid content of 45% to 60%. In some embodiments, the composition further comprises 35 to 50 weight percent of a second vegetable oil having an alpha-linolenic acid content of 45% to 55%. In some embodiments, the composition further comprises 35 to 50 weight percent of a second vegetable oil having an alpha-linolenic acid content of 45% to 50%.

In some embodiments, the composition further comprises 35 to 50 weight percent of a second vegetable oil having an alpha-linolenic acid content of 50% to 65%. In some embodiments, the composition further comprises 35 to 50 weight percent of a second vegetable oil having an alpha-linolenic acid content of 55% to 65%. In some embodiments, the composition further comprises 35 to 50 weight percent of a second vegetable oil having an alpha-linolenic acid content of 60% to 65%. In some embodiments, the composition further comprises 35 to 50 weight percent of a second vegetable oil having an alpha-linolenic acid content of 50% to 60%.

In some embodiments, the composition further comprises 0.005 to 0.1 weight percent of at least one of Vitamin A and Vitamin D. In some embodiments, the composition further comprises 0.005 to 0.05 weight percent of at least one of Vitamin A and Vitamin D. In some embodiments, the composition further comprises 0.005 to 0.01 weight percent of at least one of Vitamin A and Vitamin D.

In some embodiments, the composition further comprises 0.01 to 0.15 weight percent of at least one of Vitamin A and Vitamin D. In some embodiments, the composition further comprises 0.05 to 0.15 weight percent of at least one of Vitamin A and Vitamin D. In some embodiments, the composition further comprises 0.1 to 0.15 weight percent of at least one of Vitamin A and Vitamin D. In some embodiments, the composition further comprises 0.01 to 0.1 weight percent of at least one of Vitamin A and Vitamin D.

In some embodiments, the composition further comprises 2 to 8 weight percent of at least one phytosterol. In some embodiments, the composition further comprises 2 to 6 weight percent of at least one phytosterol. In some embodiments, the composition further comprises 2 to 4 weight percent of at least one phytosterol.

In some embodiments, the composition further comprises 4 to 10 weight percent of at least one phytosterol. In some embodiments, the composition further comprises 6 to 10 weight percent of at least one phytosterol. In some embodiments, the composition further comprises 8 to 10 weight percent of at least one phytosterol. In some embodiments, the composition further comprises 4 to 8 weight percent of at least one phytosterol. In some embodiments, the composition further comprises 4 to 5 weight percent of at least one phytosterol.

In some embodiments, the composition further comprises 0.02 to 0.15 weight percent of antioxidant. In some embodiments, the composition further comprises 0.02 to 0.1 weight percent of antioxidant. In some embodiments, the composition further comprises 0.02 to 0.05 weight percent of antioxidant. In some embodiments, the composition further comprises 0.05 to 0.2 weight percent of antioxidant. In some embodiments, the composition further comprises 0.1 to 0.2 weight percent of antioxidant. In some embodiments, the composition further comprises 0.15 to 0.2 weight percent of antioxidant. In some embodiments, the composition further comprises 0.05 to 0.15 weight percent of antioxidant.

In embodiments, the present invention is a method of treatment of oxidative stress comprising orally administering an effective amount to a human of a composition so as to result in reduction of the levels of C reactive protein (PCR), under 1.0 mg/L in blood. As used herein, "treatment of oxidative stress" may be measured by a reduction in the levels of C reactive protein (PCR), under 1.0 mg/L in a human's blood. C-reactive protein (PCR) is produced by the liver and the level of C reactive protection (PCR) rises when there is inflammation throughout the body which is related with free radicals released in oxidative processes.

In embodiments, oxidative stress is a disturbance in the prooxidant-antioxidant balance in favor of the former, leading to potential damage. Other indicators of oxidative stress may include damaged DNA bases, protein oxidation products, and lipid peroxidation products. Some conditions related to oxidative stress and cardiovascular risk are free radical accumulation (measured by a nuclear stress test), vascular inflammation (measured by echocardiogram) and general inflammation (measured by the level of C reactive protein (PCR) in the blood).

In embodiments, the effective amount for treatment of oxidative stress comprises 8 to 10 grams per dose. In embodiments, the effective amount comprises 8 to 9 grams per dose. In embodiments, the effective amount comprises 9 to 11 grams per dose. In embodiments, the effective amount comprises 10 to 11 grams per dose. In embodiments, the effective amount comprises 9 to 10 grams per dose.

In embodiments, the effective amount comprises 16 to 20 grams per day. In embodiments, the effective amount comprises 16 to 18 grams per day. In embodiments, the effective amount comprises 18 to 22 grams per day. In embodiments, the effective amount comprises 20 to 22 grams per day. In embodiments, the effective amount comprises 18 to 20 grams per day.

In embodiments, the effective amount comprises 1 dose per day. In embodiments, the effective amount comprises 2 doses per day. In embodiments, the effective amount comprises 3 doses per day. In embodiments, the effective amount comprises 4 doses per day. In embodiments, the effective amount comprises 5 doses per day. In embodiments, the effective amount comprises 6 doses per day. In embodiments, the effective amount comprises 7 doses per day. In embodiments, the effective amount comprises more than 7 doses per day.

In some embodiments, the present invention is a method of treatment of cardiovascular disease comprising orally administering an effective amount to a human of a composition so as to result in reduction of the levels of PCR, under 1.0 mg/L in blood. As used herein, "treatment of cardiovascular disease" may be measure by a reduction in the levels of C reactive protein (PCR), under 1.0 mg/L in a human's blood.

In embodiments, cardiovascular disease is the broad term for problems with the heart and blood vessels. Conditions related to cardiovascular diseases may include coronary heart disease (measured by an electrocardiogram (ECG)), heart failure (measured by an echocardiogram), arrhythmias (measured by a Holter monitor), peripheral artery disease (measured by arteriography), and/or stroke (measure by magnetic resonance angiography (MRA)).

In embodiments, the effective amount for treatment of cardiovascular disease comprises 8 to 10 grams per dose. In embodiments, the effective amount comprises 8 to 9 grams per dose. In embodiments, the effective amount comprises 9 to 11 grams per dose. In embodiments, the effective amount comprises 10 to 11 grams per dose. In embodiments, the effective amount comprises 9 to 10 grams per dose.

In embodiments, the effective amount comprises 16 to 20 grams per day. In embodiments, the effective amount comprises 16 to 18 grams per day. In embodiments, the effective amount comprises 18 to 22 grams per day. In embodiments, the effective amount comprises 20 to 22 grams per day. In embodiments, the effective amount comprises 18 to 20 grams per day.

In embodiments, the effective amount comprises 1 dose per day. In embodiments, the effective amount comprises 2 doses per day. In embodiments, the effective amount comprises 3 doses per day. In embodiments, the effective amount comprises 4 doses per day. In embodiments, the effective amount comprises 5 doses per day. In embodiments, the effective amount comprises 6 doses per day. In embodiments, the effective amount comprises 7 doses per day. In embodiments, the effective amount comprises more than 7 doses per day.

NON-LIMITING EXAMPLES

The following examples are intended to illustrate the invention and should not be construed as limiting the invention in any way.

The non-limiting examples include testing of the anti-inflammatory properties of the lipid extract CARDIOGOURMET of an embodiment of the present invention in a C. elegans model. The examples evaluate the antioxidant activity, oxidative stress and inflammatory signaling related to the lipid extract CARDIOGOURMET of an embodiment of the present invention. Moreover, the examples analyze if the molecular target of the lipid extract CARDIOGOURMET of an embodiment of the present invention is the insulin signaling pathway (IGF-1) and the transcriptional factor DAF-16, as previously described for anti-inflammatory systems.

Example 1

Antioxidant Effect

The experiments in this example were carried out by culturing synchronized nematodes age of the wild strain in different conditions N2 supply:

NG (standard culture media);
NG+ Vitamin C (positive control);
100% Ascorbic Acid;
NG+ lipid blend CONTROLG (negative control);
70-80% Canola oil, 20-30% Sunflower oil, 100-200 µg Vitamin A, 0.5-2 µg, Vitamin D and 1-3 mg Vitamin E;
NG+ lipid blend CARDIOGOURMET (compound tested); and
30-50% Canola oil, 60-70% flaxed oil, 5-10% phytosterols, 100-200 µg Vitamin A and 0.5-2 µg Vitamin D.

The compositions of CARDIOGOURMET and CONTROL G are detailed in Tables 1 and 2.

TABLE 1

CARDIOGOURMET

| Raw Material | % |
|---|---|
| Canola oil | 46.59 |
| Flax seed oil | 45.30 |
| Phytosterols | 8.00 |
| Rosemary Extract | 0.10 |
| Vitamin A and D | 0.01 |

TABLE 2

CONTROL G

| Raw Material | % |
|---|---|
| Canola Oil | 60.00 |
| Sunflower oil | 39.95 |
| Alpha-Tocopherol | 0.04 |
| Vitamin A and D | 0.007 |
| TBHQ (antioxidant) | 0.0012 |

In this example, worms were incubated at 20° C. and after 5 days were subjected to an oxidative stress with hydrogen peroxide at 2 mM for 5 hours. A survival count was then performed on each condition.

Five different concentrations of each sample (CONTROL G and CARDIOGOURMET) were tested at 0.01 mg/mL, 0.06 mg/mL, 0.1 mg/mL, 1 mg/mL and 10 mg/mL. The antioxidant activity in *C. elegans*. survival rate after oxidative stress with hydrogen peroxide at 2 mM of each sample is shown in FIG. 2.

Figure 2:
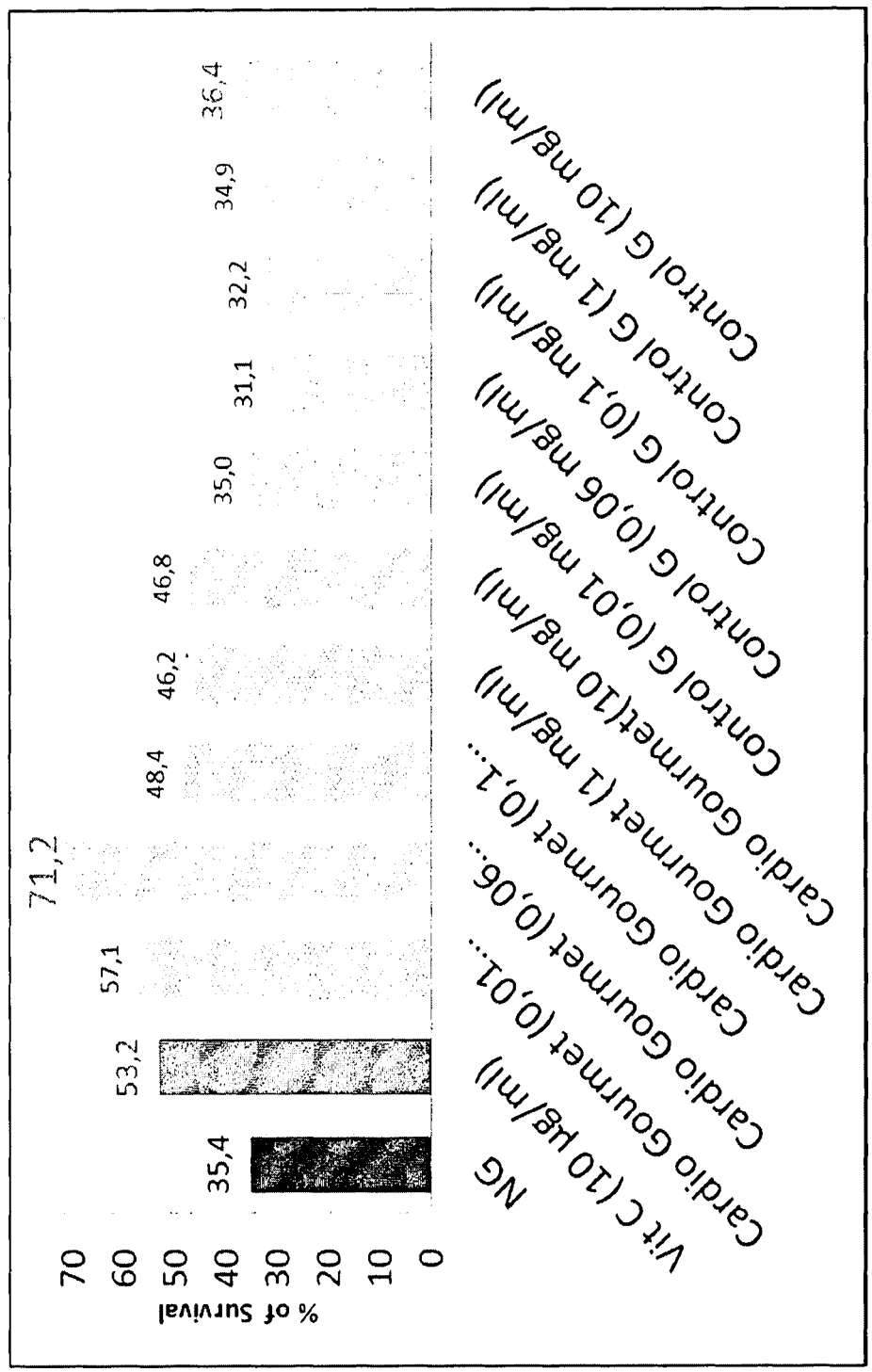
FIG. 2 illustrates results of survival rates to acute oxidative stress of Caenorhabditis elegans (C. elegans) when treated with CARDIOGOURMET at different concentrations.
Figure 3:
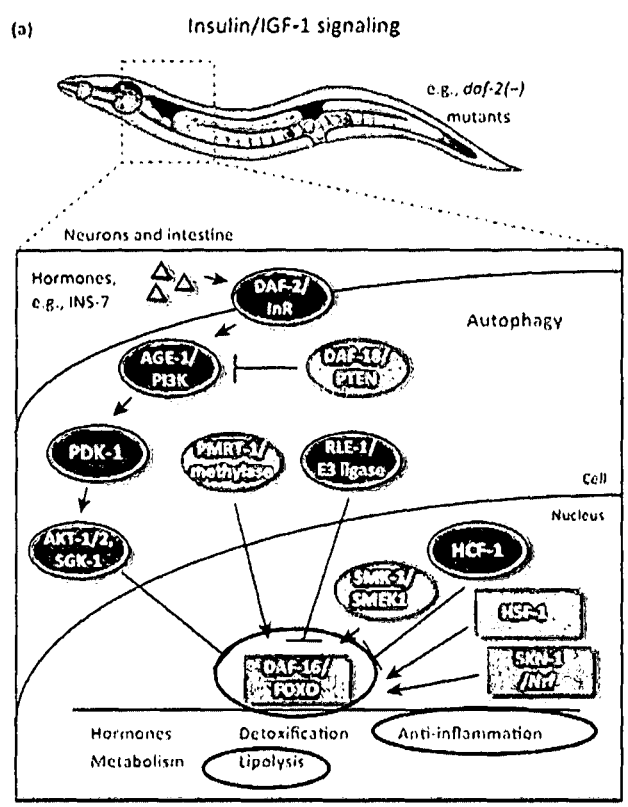
FIG. 3 illustrates Insulin/IGF-1-regulated pathway in C. elegans strain mutant in DAF-16.

As noted in FIG. 2, an antioxidant effect with CARDIOGOURMET was observed as illustrated by increased nematode survival after acute oxidative stress. In contrast, no antioxidant effect was observed in the case of the CONTROL G.

Example 2

Molecular Pathway

An additional experiment was conducted with *C. elegans* strain DAF-16 IIS-regulated mutant. Life expectancy tests were performed on two conditions: NG (control) and CARDIOGOURMET. As noted in FIG. 2, the highest survival rate occurred in example 1 with a dose of 0.06 mg/ml of CARDIOGOURMET. Accordingly, a dose of 0.06 mg/ml of CARDIOGOURMET was also used for this example.

Survival curves where examined to assess if the sample produces an increase in the longevity of DAF-16 mutants. The results of assessment then suggest whether the condition acts to modulate the activity of the IIS path and thus, has anti-inflammatory activity and thus, would potentially be effective in the treatment of oxidative stress and/or cardiovascular disease.

Acute oxidative stress tests performed with N2 and DAF-16 mutant strains used hydrogen peroxide at 1.75 mM. The effect of total loss of antioxidant protective phenotype in the mutant strain in DAF-16 in the presence of CARDIOGOURMET is shown in FIG. 4.

Figure 4:
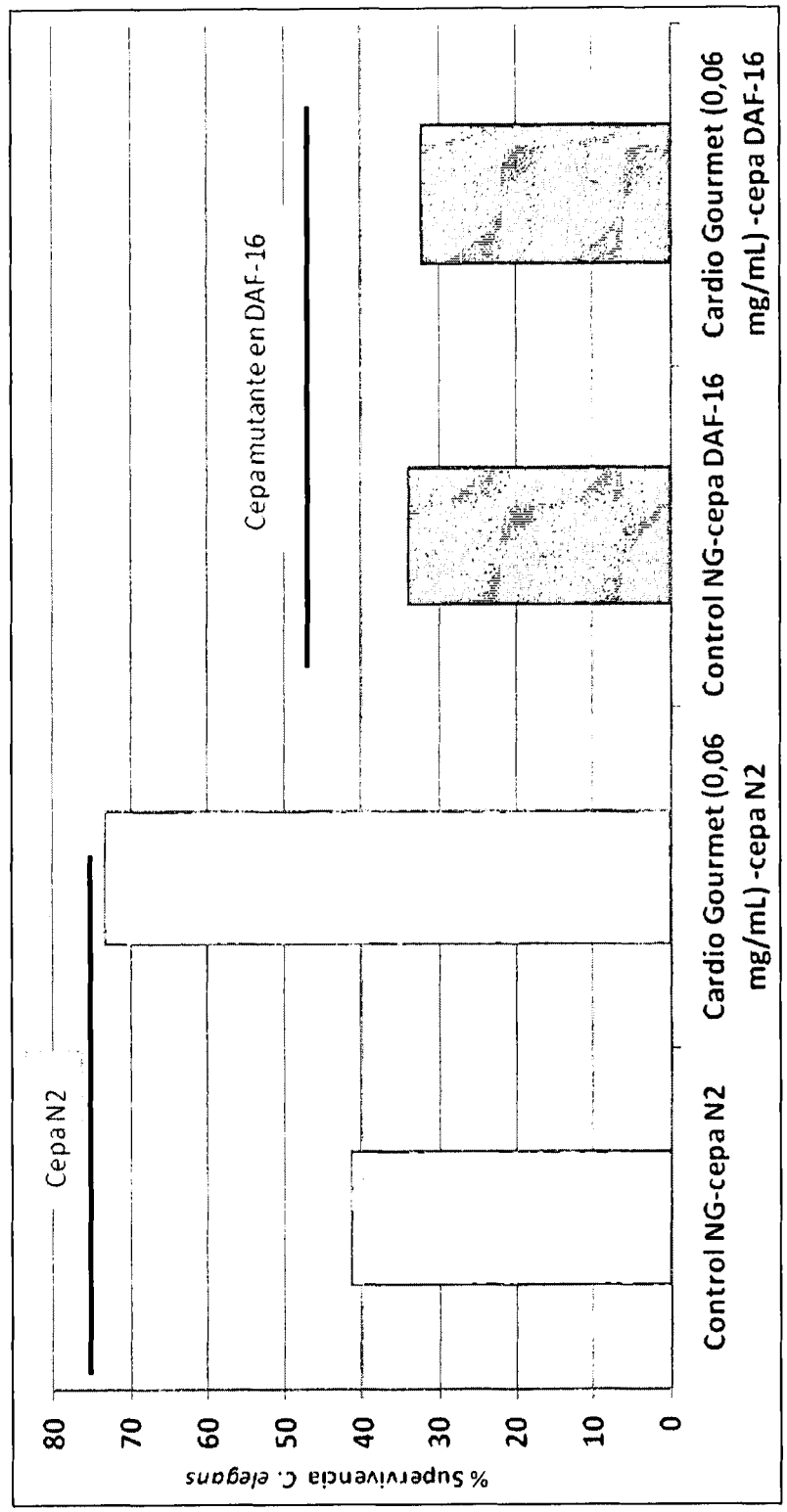
FIG. 4 illustrates results of survival rate to acute oxidative stress of C. elegans strain mutant in DAF-16 when treated with CARDIOGOURMET.

As shown in FIG. 4, CARDIOGOURMET exhibited a complete loss of antioxidant protective phenotype mutant strain in DAF-16. The results suggest CARDIOGOURMET exhibits antioxidant activity and may require transcriptional factor for such activity. The results further illustrate the anti-inflammatory potential of CARDIOGOURMET and thus, the potential effectiveness for treatment of oxidative stress and/or cardiovascular disease.

Example 3

Reduction of Corporal Fat

Figure 5:
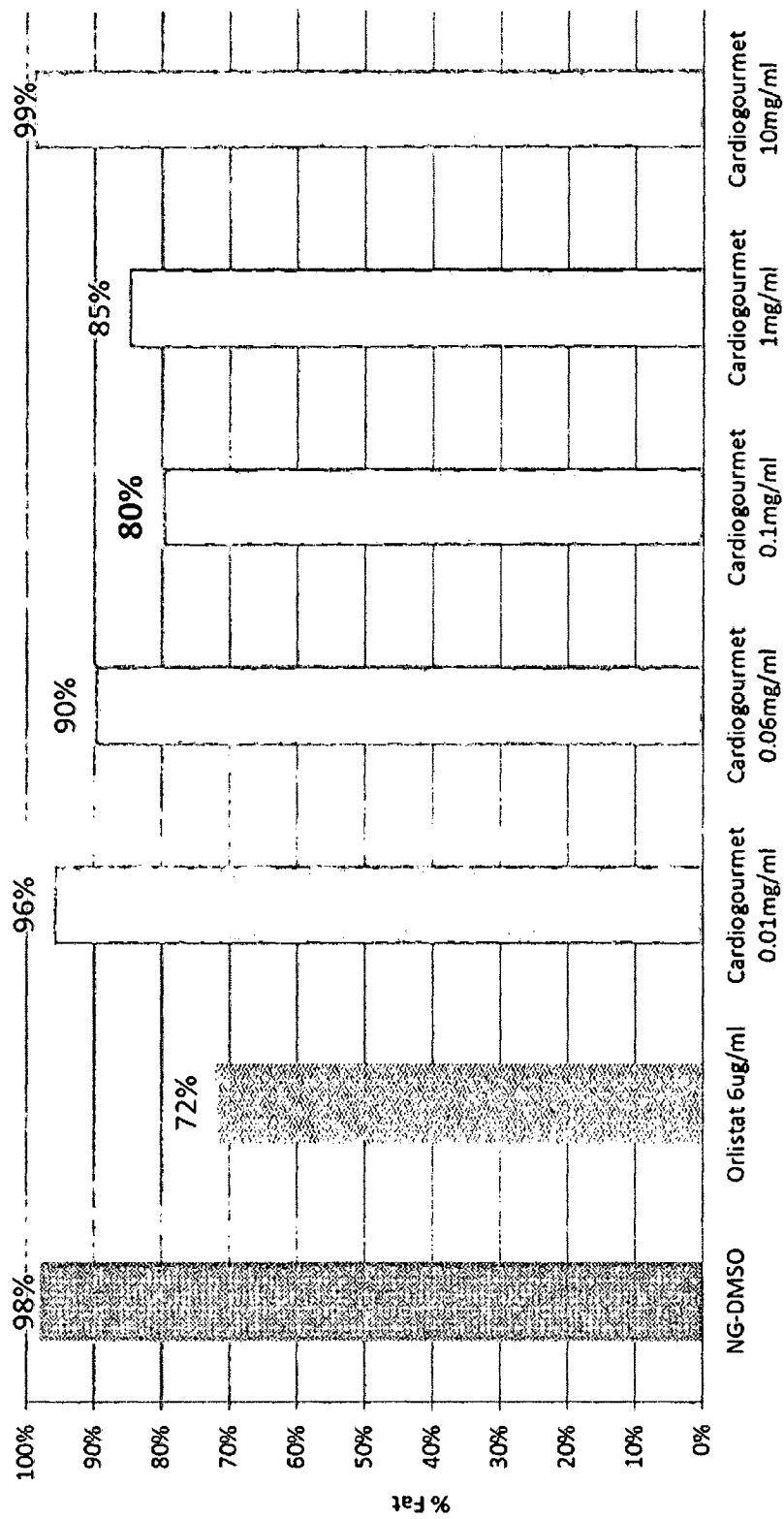
FIG. 5 illustrates measurements of body fat in C. elegans strain NG when treated with CARDIOGOURMET at different concentrations.

Assays for measuring body fat in *C. elegans* were done by staining with Nile Red (λ ex 480 nm. λ Em 571 nm). This example was carried out by culturing synchronized nematodes age of the N2 strain NG (negative control) medium supplemented with CARDIOGOURMET (at the five concentrations detailed in Example 1). Fat quantification was performed in young adults by measuring fluorescence in a spectrofluorimeter. The relative percentage of fluorescence was determined in the CARDIOGOURMET versus control nematodes:

NG– DMSO
NG+ Orlistat (positive control)
100% tetrahydrolipstatin
NG+ lipid blend CARDIOGOURMET (compound tested)
30-50% Canola oil, 60-70% flaxseed oil, 5-10% phytosterols, 100-200 µg Vitamin A and 0.5-2 µg Vitamin D The dose of 0.1 mg/mL (FIG. 5) causes a reduction of 20% of the fat in the nematode (relative to normal conditions NG DMSO which result in only a 2% reduction in the nematode fat) and thus, shows potential effectiveness for treatment of oxidative stress and/or cardiovascular disease.

Figure 6:
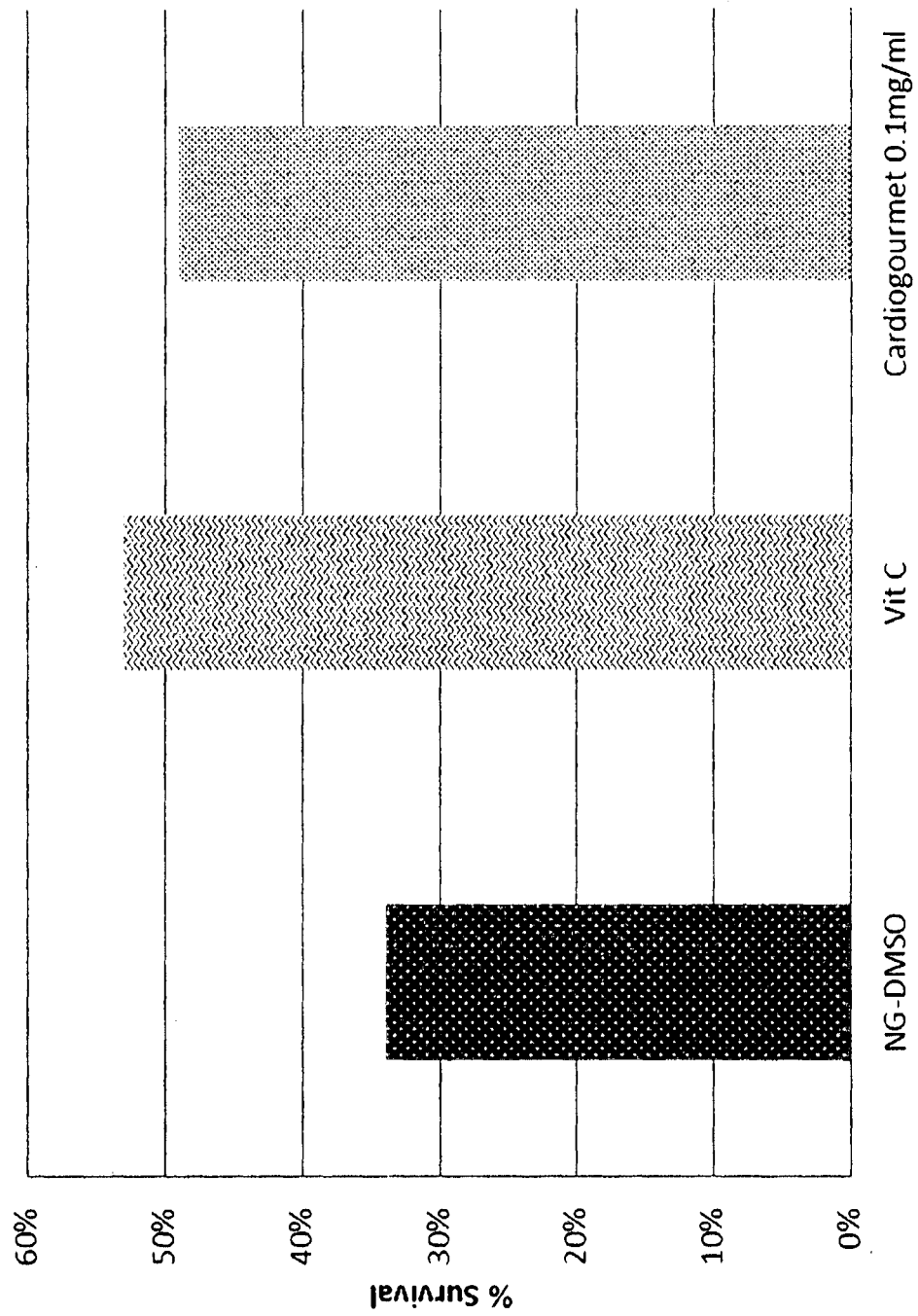
FIG. 6 illustrates results of survival rate to acute oxidative stress of C. elegans strain NG when treated with CARDIOGOURMET at a dose of 0.1 mg/mL.

This dose also produced an antioxidant effect as illustrated by an increase of 13% survival in *C. elegans* as shown in FIG. 6 and thus, shows potential effectiveness for treatment of oxidative stress and/or cardiovascular disease.

Additional Details Regarding Application of *C. elegans* Model

*C. elegans* is a free-living nematode, approximately 1 mm in length, which exists as either a self-fertilizing hermaphrodite or as a male. *C. elegans* genome has been fully sequenced which has revealed that about 80% of *C. elegans* genes have human homologs and at least 42% of human disease-related genes have a *C. elegans* homolog.

The nematode *Caenorhabditis elegans* has become established as a major experimental organism with applications to many biomedical research areas. The body wall muscle cells are a useful model for the study of human cardiomyocytes and their homologous structures and proteins. Because of the small size of this nematode (1-mm-long adults), a heart and circulatory system are not required. The close homology of proteins and structures of interest justify the study of nematode body wall muscle as a way to understand human heart muscle.

In addition, *C. elegans* has become an excellent model for screening of compounds for therapeutic purposes. Regarding inflammation, *C. elegans* has recently been used to study an anti-inflammatory non-steroidal: Celecoxib®. The results showed that the drug requires the activity of DAF-16, FOX ( )transcription factor that regulates longevity in response to the signaling pathway insulin/IGF-I (IIS). All this suggests that IIS is a key target for the search for compounds with potential anti-inflammatory properties. FIG. 7 illustrates some additional features of the *C. elegans* model.

Example 4

The ability of the one embodiment of the composition of the present invention to treat oxidative stress and/or cardiovascular disease in human subjects is evaluated in this example. Human subjects are treated with a composition detailed in Table 3.

TABLE 3

CARDIOGOURMET

| Raw Material | % |
|---|---|
| Canola oil | 46.59 |
| Flax seed oil | 45.30 |
| Phytosterols | 8.00 |
| Rosemary Extract | 0.10 |
| Vitamin A and D | 0.01 |

The treatment regimen is 9 grams per dose and 2 doses per day. The levels of C reactive protein (PCR) in the human subject's blood are measured before and after treatment. Treated humans show a reduction in the levels of C reactive protein (PCR) to under 1.0 mg/L in the treated human subject's blood compared to a non-treated human or the human subject before treatment. Thus, the example shows treatment of cardiovascular disease and oxidative stress in the treated human subject compared to a non-treated human or the human subject before treatment.

While a number of embodiments of the present invention have been described, it is understood that these embodiments are illustrative only, and not restrictive, and that many modifications may become apparent to those of ordinary skill in the art. Further still, the various steps may be carried out in any desired order (and any desired steps may be added and/or any desired steps may be eliminated).

We claim:

1. A composition comprising:
   - 35 to 50 weight percent of a first vegetable oil having a saturated fatty acid content of 4% to 12%;
   - (ii) 35 to 50 weight percent of a second vegetable oil having an alpha-linolenic acid content of 45% to 65%;
   - (iii) 0.005 to 0.15 weight percent of Vitamin A and Vitamin D;
   - (iv) 2 to 10 weight percent of phytosterols; and,
   - (v) 0.02 to 0.2 weight percent of an antioxidant.

2. The composition of claim 1, wherein the composition comprises 40 to 50 weight percent of the first vegetable oil.

3. The composition of claim 1, wherein the composition comprises 40 to 50 weight percent of the second vegetable oil.

4. The composition of claim 1, wherein the composition comprises 5 to 10 weight percent of the phytosterols.

5. The composition according to claim 1, wherein the composition comprises 0.1 to 0.2 weight percent of the antioxidant.

6. The composition according to claim 1, wherein a therapeutically effective amount of the composition that is administered to a subject in need thereof can treat oxidative stress.

7. The composition according to claim 1, wherein a therapeutically effective amount of the composition that is administered to a subject in need thereof can treat a cardiovascular disease.

8. The composition according to claim 6, wherein the therapeutically effective amount of the composition reduces the levels of C reactive protein (PCR) under 1.0 mg/L blood.

9. The composition according to claim 7, wherein the therapeutically effective amount of the composition reduces the levels of C reactive protein (PCR) under 1.0 mg/L blood.

* * * * *